(12) United States Patent
Oue et al.

(10) Patent No.: US 8,485,842 B2
(45) Date of Patent: Jul. 16, 2013

(54) CONNECTOR

(75) Inventors: Takeshi Oue, Hino (JP); Masanori Suzuki, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/489,540

(22) Filed: Jun. 6, 2012

(65) Prior Publication Data

US 2012/0329312 A1 Dec. 27, 2012

Related U.S. Application Data

(63) Continuation of application No. PCT/JP2011/078049, filed on Dec. 5, 2011.

(30) Foreign Application Priority Data

Dec. 6, 2010 (JP) .................................. 2010-271677

(51) Int. Cl.
*H01R 13/72* (2006.01)

(52) U.S. Cl.
USPC .............................. 439/501; 439/452; 439/459

(58) Field of Classification Search
USPC .................. 439/445, 446, 452, 459, 460, 501
See application file for complete search history.

(56) References Cited

U.S. PATENT DOCUMENTS

| 936,156 | A | * | 10/1909 | Parker | 24/136 R |
| 1,961,013 | A | * | 5/1934 | Saraceno | 439/446 |
| 3,794,960 | A | * | 2/1974 | Sugar | 439/459 |
| 4,575,174 | A | * | 3/1986 | Leeds et al. | 439/465 |
| 4,761,145 | A | * | 8/1988 | Goto et al. | 439/469 |
| 6,220,889 | B1 | * | 4/2001 | Ely et al. | 439/446 |
| 7,112,086 | B1 | * | 9/2006 | Wu | 439/460 |
| 7,959,459 | B2 | * | 6/2011 | Mundt | 439/501 |
| 2002/0098732 | A1 | | 7/2002 | Shimizu | |
| 2010/0197165 | A1 | * | 8/2010 | Mundt | 439/501 |
| 2010/0279518 | A1 | * | 11/2010 | Watanabe et al. | 439/40 |
| 2011/0165791 | A1 | * | 7/2011 | Lu | 439/485 |
| 2012/0329312 | A1 | * | 12/2012 | Oue et al. | 439/452 |

FOREIGN PATENT DOCUMENTS

| JP | 08-036139 | 2/1996 |
| JP | 2002-214538 | 7/2002 |

* cited by examiner

*Primary Examiner* — James Harvey

(74) *Attorney, Agent, or Firm* — Scully, Scott, Murphy & Presser, P.C.

(57) ABSTRACT

A connector includes an electric cable, an electric connecting portion that includes a case body in a rectangular shape and a circuit board, and has, on the circuit board, a line connecting portion electrically connected to a line of the electric cable, and a cable fixing portion to which the electric cable is fixed, a flat-type connector case that has a housing space housing the electric connecting portion and the electric cable, an opening in which the case body is integrally mounted, and an extension hole from which the electric cable is extended into the housing space, and is fixed to an intermediate portion of the electric cable, and a slide member that is slidably disposed in the housing space, and includes, on one surface side, a cable bending shape defining portion that defines a bending shape of the electric cable which is housed in the housing space.

7 Claims, 10 Drawing Sheets

CONNECTOR

CROSS REFERENCE TO RELATED APPLICATION

This application is a continuation application of PCT/JP2011/078049 filed on Dec. 5, 2011 and claims benefit of Japanese Application No. 2010-271677 filed in Japan on Dec. 6, 2010, the entire contents of which are incorporated herein by this reference.

BACKGROUND OF THE INVENTION

1. Field of the Invention

The present invention relates to a connector, and particularly to a connector which is configured with a cable which is extended by a predetermined length from an opening of a flat-type connector case, the cable being housed in the connector case.

2. Description of the Related Art

A connector is used for simultaneously connecting a plurality of wirings connecting an apparatus and peripheral equipment of the apparatus. For example, Japanese Patent Application Laid-Open Publication No. 8-36139 discloses an electronic endoscope connector including a shield case.

In the electronic endoscope connector, a terminal portion is taken out from a connector case of an integral structure, and thereafter, a shield case can be extracted from an inside of the connector case. Subsequently, the shield lid body is taken out from the shield main body of the extracted shield case, whereby the circuit board can be exposed. The electronic endoscope connector has the configuration in which the signal cable is wound twice or more around the inner portion of the ferrite core which removes high frequency noise in order to carry out noise control measures.

In recent years, in place of a signal cable which requires noise control measures by a ferrite core or the like, an electric cable which is given a noise control function has been used. The electric cable having a noise control function is configured by further including, for example, a ferrite compound layer, an insulating coating layer and the like, with which the shield layer is covered, in addition to the shield layer with which the signal lines are covered. Therefore, in the electric cables having the noise control functions, sturdiness to keep a linear state becomes high, though flexibility is obtained.

If the signal cable of the electronic endoscope connector of the aforementioned Japanese Patent Application Laid-Open Publication No. 8-36139 is changed to an electric cable given the noise control function, the sturdiness of the electric cable becomes strong, though the ferrite core is not required.

SUMMARY OF THE INVENTION

A connector in one mode of the present invention includes an electric cable, an electric connecting portion that includes a case body in a rectangular shape and a circuit board, and has, on the circuit board, a line connecting portion electrically connected to a line inserted through an inside of the electric cable, and a cable fixing portion to which a distal end portion of the electric cable is fixed, a flat-type connector case that has a housing space housing the electric connecting portion and the electric cable, an opening in which the case body of the electric connecting portion is integrally mounted, and an extension hole from which the cable is extended into the housing space, and is fixed to an intermediate portion of the electric cable, and a slide member that is slidably disposed in the housing space of the connector case, and includes, on one surface side, a cable bending shape defining portion that defines a bending shape of the electric cable which is housed in the housing space.

A connector in another mode of the present invention includes a cable portion group including a connector case in a flat shape that is fixed to an intermediate portion of an electric cable, and at least one cable side connector electrically connected to a line inserted through an inside of the electric cable extended by a predetermined length from an opening in a rectangular shape via a housing space included by the connector case, a terminal portion group including a case body in a rectangular shape fixedly provided in the opening, and a board mounting a board-side connector to which the cable-side connector is connected, and having a cable fixing portion to which a distal end portion of the electric cable is fixed, and a slide member that is slidably disposed in the housing space of the connector case, and includes a cable bending shape defining portion that deforms the electric cable in a state in which the cable-side connector is connected to the board side connector of the board, into a predetermined bending shape and houses the electric cable in the housing space.

DETAILED DESCRIPTION OF THE PREFERRED EMBODIMENT

Hereinafter, an embodiment of the present invention will be described with reference to the drawings.

Figure 1:
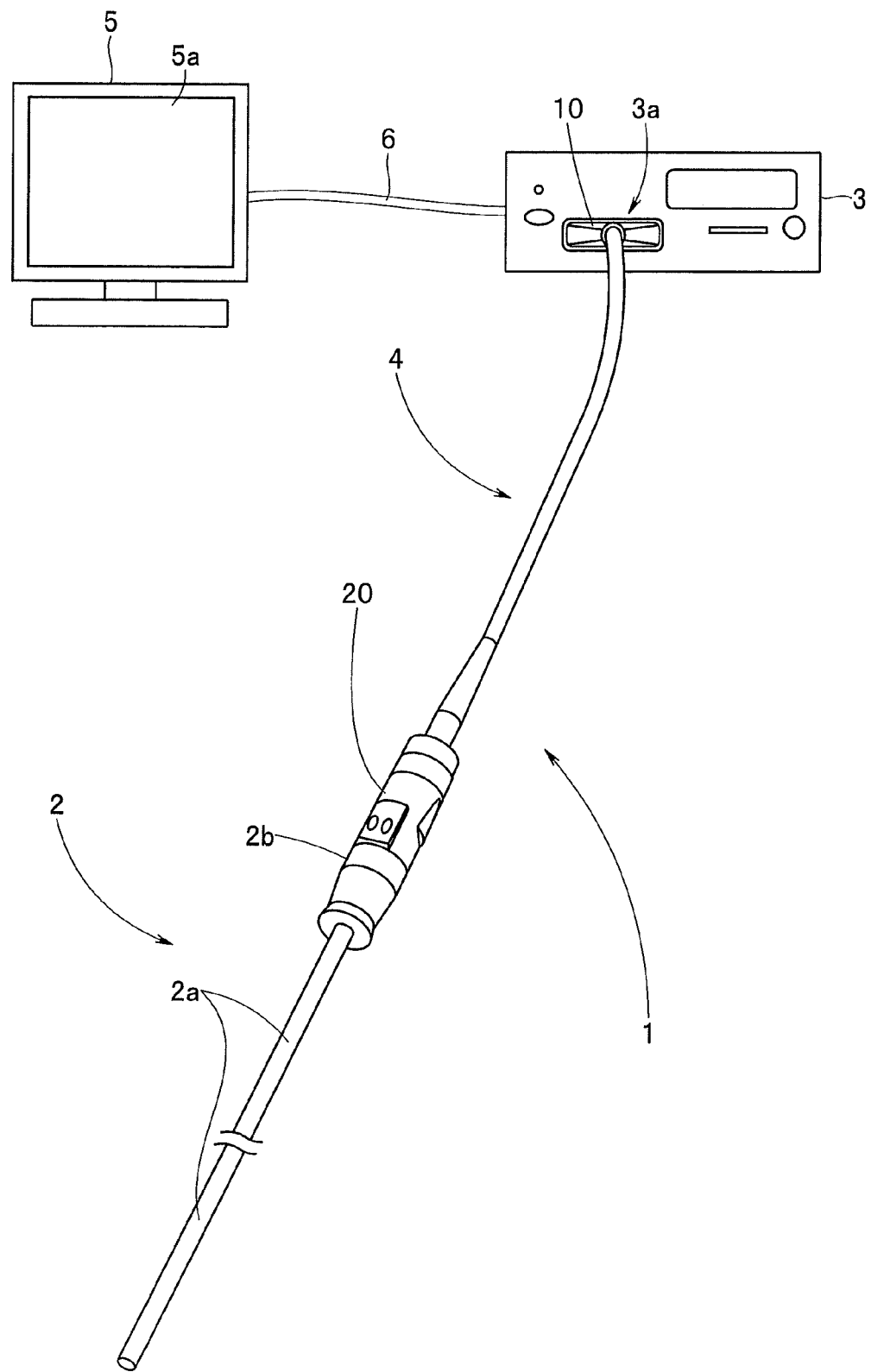
FIG. 1 is a view showing an endoscope system in which a rigid endoscope and a video processor are connected by a connection cable.

As shown in FIG. 1, a connector 10 of the present invention is provided at one end side of a connection cable 4. The connection cable 4 connects, for example, a rigid endoscope (hereinafter, described as a rigid endoscope) 2 which is an apparatus, and a video processor 3 which is peripheral equipment of the rigid endoscope 2.

Reference sign 1 designates an endoscope system. The endoscope system 1 is configured by including the rigid endoscope 2, the video processor 3, the connection cable 4 and a display apparatus 5.

The rigid endoscope 2 includes a relay lens (not illustrated) in an insertion portion 2a. The video processor 3 includes a connector connecting portion 3a, and includes a control section, a signal processing circuit and the like which are not illustrated inside the apparatus.

Reference sign 2b designates a camera connecting portion. A second connector 20 which the connection cable 4 includes is connected to the camera connecting portion 2b. Reference sign 6 designates a video cable. The video cable 6 connects the video processor 3 and the display apparatus 5.

Figure 2A:
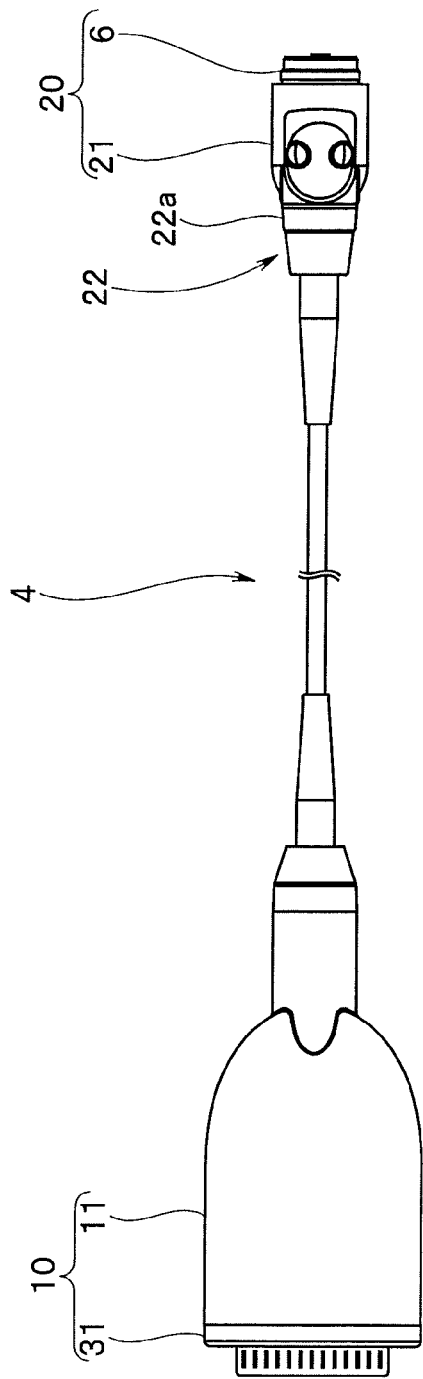
FIG. 2A is a plan view explaining a configuration of the connection cable.
Figure 2B:
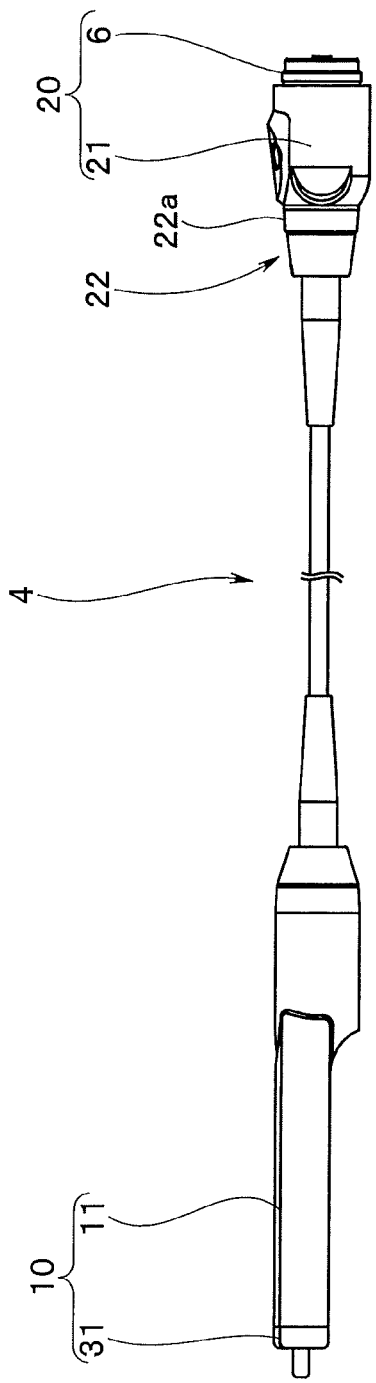
FIG. 2B is a side view explaining the configuration of the connection cable.

As shown in FIGS. 2A and 2B, the connection cable 4 includes the first connector 10 and the second connector 20. The first connector 10 is configured by a terminal portion 31, which is a case body, being integrally fixed to a flat-type first connector case 11. The second connector 20 is configured by a camera apparatus 6 being integrally fixed to, for example, a round-type second connector case 21. In the present embodiment, the second connector 20 is a camera apparatus.

According to the present embodiment, the first connector 10 of the connection cable 4 is connected to the connector connecting portion 3a, and the second connector 20 is connected to the camera connecting portion 2b, as shown in FIG. 1. As a result, an optical image which is captured by the rigid endoscope 2 is displayed on a screen 5a of the display apparatus 5 as an endoscopic image.

The second connector 20 is configured by the second connector case 21 and a second case connecting member 22. The second case connecting member 22 is provided with a connector discrimination portion 22a. The connector discrimination portion 22a notifies a user of the kind of the connector which the connection cable has by difference in color.

The connector discrimination portion 22a is integrally provided at the second case connecting member 22 by integral molding. The connector discrimination portion 22a of the present embodiment is molded of the same material as the second case connecting member 22 in a different color, for example, a blue color in advance as an integrally molded insert component. Subsequently, the connector discrimination portion 22a is disposed in a metal mold as an insert component when the second case connecting member 22 is molded of the same material in a black color, for example.

As a result, the second case connecting member which has the connector discrimination portion is formed of the same material without mixture of resins. The second case connecting member which is configured as above contributes to reduction in the number of components, and reduction in the number of assembly processes.

The second connector 20 included in the connection cable 4 may be a connector or the like which is connected to another apparatus, or another peripheral apparatus without being limited to a camera apparatus. Further, in the present embodiment, a configuration in which the first connector 10 is provided at one end side of the connection cable 4 is shown. However, a configuration in which the first connectors 10 are provided at both ends of the connection cable, or a configuration in which the first connector 10 is provided at an end portion of the cable which is extended from an apparatus may be adopted.

Here, the configuration of the cable having the first connector 10 at one end portion will be described.

Figure 3:
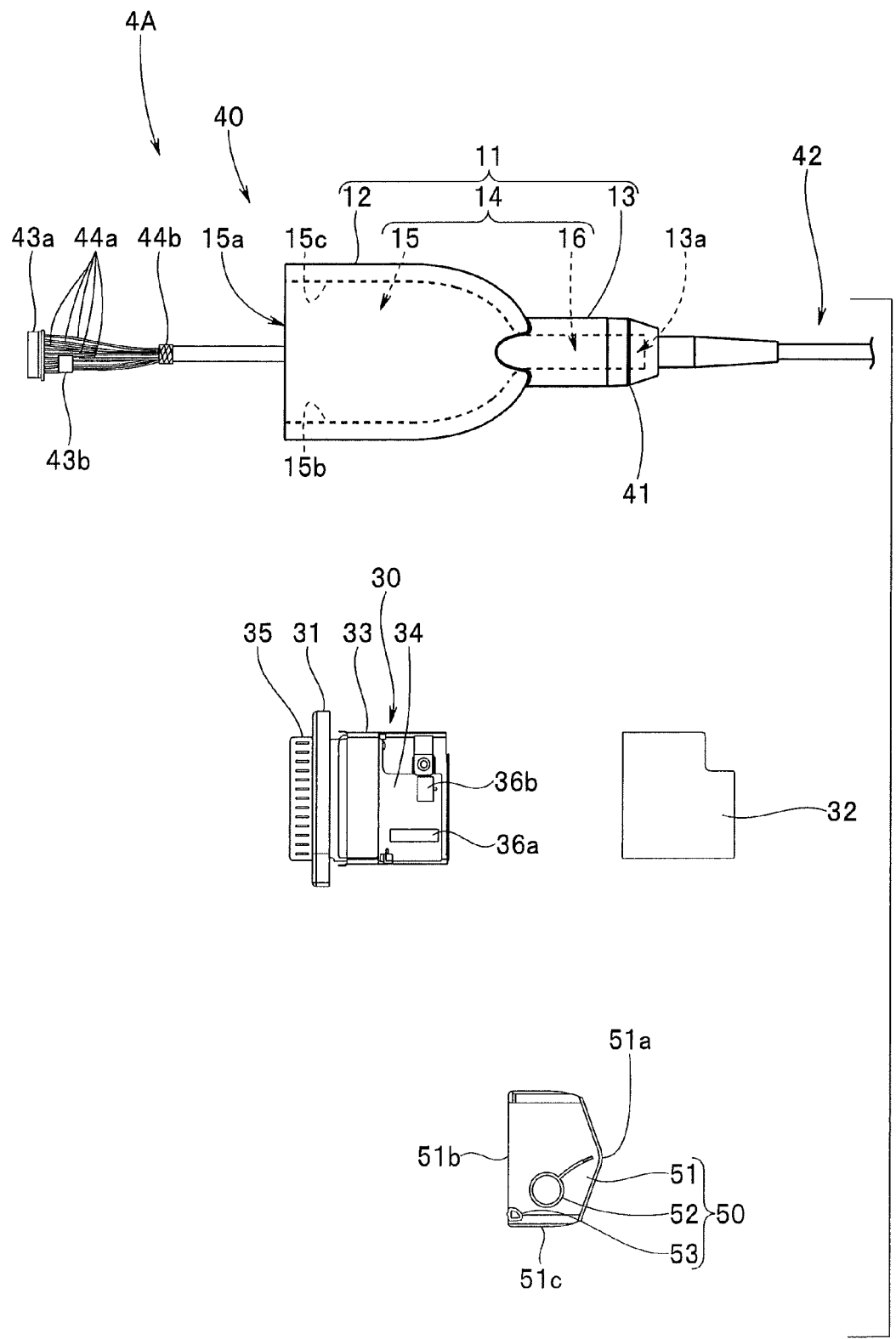
FIG. 3 is a view showing respective portions configuring the cable.

A cable 4A of the present embodiment includes the first connector 10 at an end portion of the cable which is extended from the apparatus, for example. As shown in FIG. 3, the cable 4A is configured by including a terminal portion group 30, a cable portion group 40, and a slide member 50. Reference sign 32 designates a shield cover which will be described later, and configures the terminal portion group 30.

With reference to FIGS. 3 to 6, the cable portion group 40 will be described.

Figure 6:
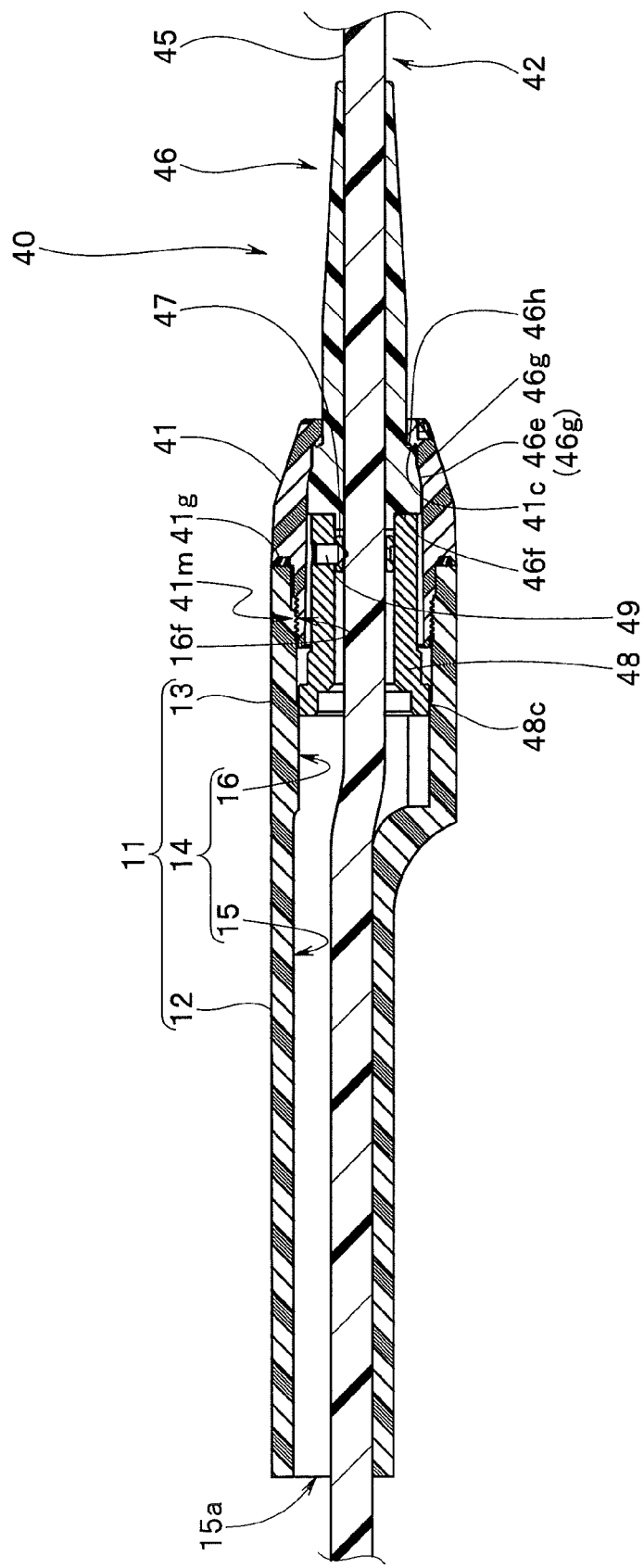
FIG. 6 is a view explaining a cable portion group with the connector case integrally and water-tightly fixed to an end portion of the cable and the cable of a predetermined length extended from an opening of the connector case.

As shown in FIGS. 3 and 6, the cable portion group 40 includes a first case connecting member 41, a bend preventing integral cable (hereinafter, abbreviated as an integral cable) 42, and a first connector case 11.

The first connector case 11 is formed of, for example, a rigid resin member. The first connector case 11 includes a housing portion 12 and a connecting portion 13, and is provided with a space portion 14 inside the case.

The space portion 14 is configured by including a first housing space 15 and a second housing space 16. The housing portion 12 is in a flat shape, and has a shield case housing region (reference sign 15d of FIG. 11C) and a slide member housing region (reference sign 15e of FIG. 11C). A shield case, which will be described later, is housed in the shield case housing region 15d. An electric cable 45 that configures the integral cable 42, which will be described later, is housed in the slide member housing region 15e so as to be bent in a substantially S-shape. The first housing space 15 includes an opening 15a in a rectangular shape.

Meanwhile, the connecting portion 13 is in a tube shape, and includes an extension hole 13a which allows the electric cable 45 to extend in the first housing space 15. Reference sign 16f is a female screw portion which is provided on an inner surface of the second housing space 16.

In the present embodiment, the first connector case 11 and the first case connecting member 41 are integrally connected by being screwed together. In the integrated state, the first connector case 11 is integrally fixed to a bend preventing portion, which will be described later, of the integral cable 42 with water tightness being kept.

In the present embodiment, a length of the electric cable 45 is set to be extended from a case opening side end surface of the first connector case 11 by a predetermined length in consideration of operability and housing easiness.

Reference signs 43a and 43b designate cable-side connectors, and are, for example, male connectors. In the male connectors 43a and 43b, a plurality of signal lines 44a which are inserted through an inside of the integral cable 42, are wired at predetermined positions. Reference sign 44b designates shield members with which the plurality of signal lines 44a are covered, and which are combined into one and tidied up at a distal end portion of the integral cable 42.

Figure 4:
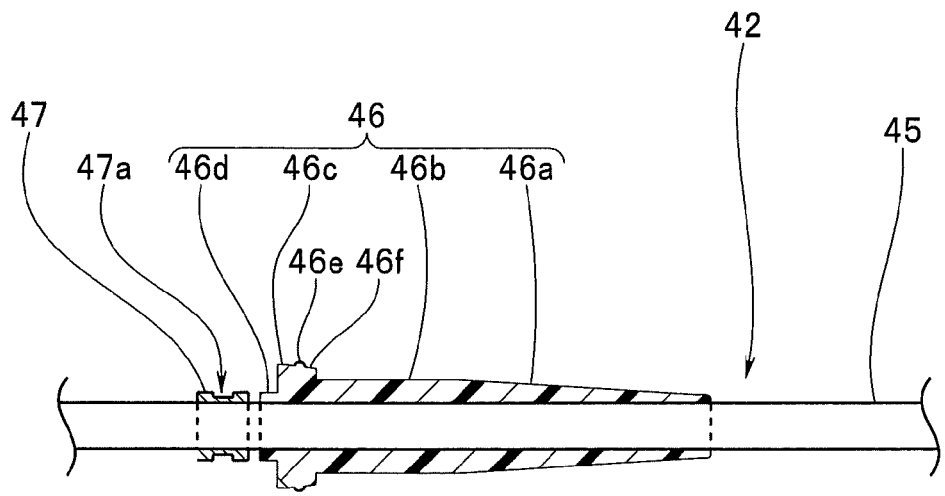
FIG. 4 is a view explaining a bend preventing portion integrated with the cable.

As shown in FIG. 4, the integral cable 42 is configured such that a bend preventing portion 46 is integrally provided fixedly at an intermediate portion of the electric cable 45 which is given a noise control function.

The bend preventing portion 46 is set to have a predetermined length dimension. The bend preventing portion 46 includes, for example, a taper surface 46a, a tubular portion 46b, a protruded portion 46c and a projected portion 46d. The bend preventing portion 46 is made of a resin or an elastic rubber which has a predetermined elasticity. The bend preventing portion 46 is integrally provided at a predetermined position by integral molding to an outer sheath of the electric cable 45.

More specifically, in the present embodiment, the electric cable 45 is handled as an insert component, whereby the bend preventing portion 46 is integrally provided at the electric cable 45.

Reference sign 46e designates an outer circumferential protruded portion. The outer circumferential protruded portion 46e is circumferentially provided on, for example, an outer circumferential slant surface 46f included by the protruded portion 46c. The outer circumferential protruded portion 46e is, for example, semi-circular in section, and a radial dimension thereof is set in consideration of water tightness.

A fixing section 47 is a ring member of a metal, and includes a circumferential groove 47a in a center in a longitudinal direction of an outer circumferential face. The fixing section 47 is disposed on the outer circumferential face in a vicinity of the projected portion 46d of the bend preventing portion 46 which is integrally provided on the electric cable 45, and is integrally fixed to the cable outer circumferential face by crimping fixation.

The electric cable 45 is configured by being further provided with, for example, a ferrite compound layer (not illustrated), and an insulating coating layer (not illustrated), in addition to the plurality of signal lines 44a and the shield member 44b which configures the shield layer with which these signal lines 44a are covered.

The electric cable 45 which is configured as above has an irradiation noise reduction effect equivalent to or more than when straightly passing the signal cable configured by including the plurality of signal lines and the shield layer covering the signal lines through a ferrite core. However, the electric cable 45 has strong sturdiness to keep a straight state, although flexibility is obtained. Therefore, in the electric cable 45, it becomes difficult to keep a sagging state like a signal cable.

Figure 5:
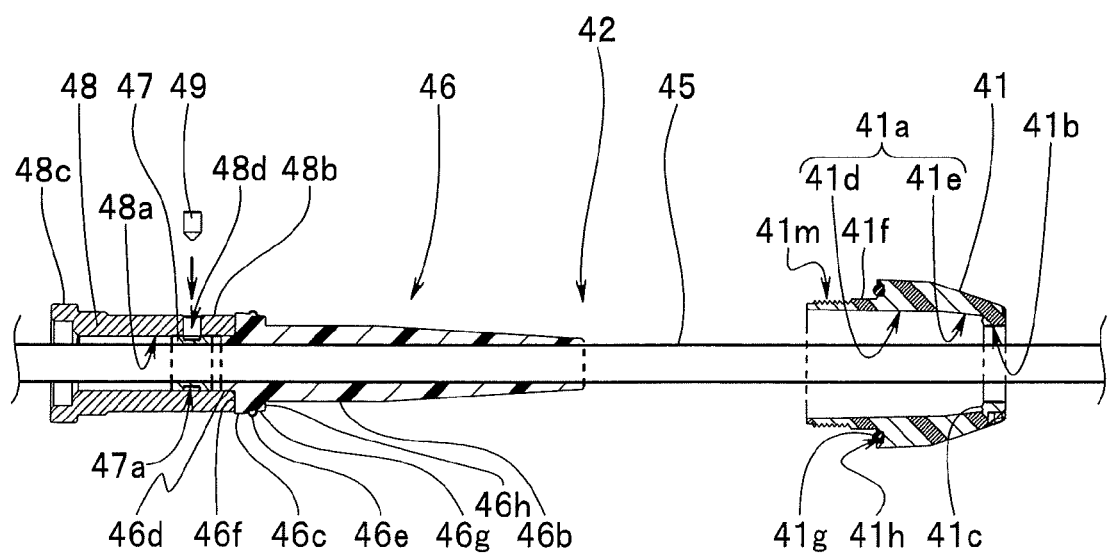
FIG. 5 is a view explaining a configuration for integrally and water-tightly fixing a connector case to the cable.

As shown in FIG. 5, a support member 48 is disposed at the fixing section 47 side of the electric cable 45. The first case connecting member 41 is disposed at an opposite side thereof with the fixing section 47 and the bend preventing portion 46 therebetween.

The support member 48 is a tubular member of a metal. The support member 48 has a through hole 48a in an axial direction, and includes a small diameter portion 48b and a large diameter portion 48c on an outer circumference. Reference sign 48d designates a pin hole, in which a crimping pin 49, which will be described later, is disposed. The pin hole 48d allows the through hole 48a to communicate with an outside. The pin hole 48d is formed at a position apart from an end surface of the small diameter portion 48b by a predetermined distance.

An inside diameter dimension of the through hole 48a is set to be engaged with the outer circumferential face of the fixing section 47 by predetermined fitting. An outside diameter of the small diameter portion 48b is set to be smaller by a predetermined dimension than an outside diameter of the protruded portion 46c. An outside diameter of the large diameter portion 48c is larger than the outside diameter of the protruded portion 46c, and is set so that an inner surface of the second housing space 16 is engaged therewith as a predetermined fitting manner.

The support member 48 is integrally mounted to the fixing section 47 by the crimping pin 49 in a state in which the support member 48 is disposed on the outer circumferential face of the fixing section 47. More specifically, the circumferential groove 47a is disposed directly under the pin hole 48d of the support member 48, and in the state, the crimping pin 49 is inserted and disposed in the pin hole 48d. Thereafter, a head portion of the crimping pin 49 is hit, and the crimping pin 49 is press-fitted and disposed in the circumferential groove 48a and the pin hole 48d. Thereby, the support member 48 is integrally fixed to the fixing section 47 integrated with the electric cable 45. In the fixed state, a bend preventing portion side end surface of the support member 48 is disposed to abut on an end surface 46f which is formed by the protruded portion 46c and the projected portion 46d.

The first case connecting member 41 is formed of, for example, a rigid resin member into a cylindrical shape. The first case connecting member 41 includes a recessed portion 41a. The recessed portion 41a and an outside communicate with each other by an axial direction through hole 41b formed on a bottom surface. An inside diameter of the axial direction through hole 41b is set to be larger by a predetermined dimension than an outside diameter dimension of the tubular portion 46b.

An annular protruded portion 41c is formed on the bottom surface of the recessed portion 41a on which the axial direction through hole 41b is formed. The annular protruded portion 41c abuts on a raised surface 46h of the tubular portion 46b and the outer circumferential slant surface 46g. The annular protruded portion 41c is provided to be located in a substantially middle of an outside diameter of the axial direction through hole 41b and an inner surface of the recessed portion 41a. A cross-sectional shape of the annular protruded portion 41c is, for example, an angular shape, or a semicircular shape, and a height dimension thereof is set in consideration of water tightness.

The recessed portion 41a includes a first disposition portion 41d and a second disposition portion 41e. In the first disposition portion 41d, the support member 48 and the protruded portion 46c are disposed. The second disposition portion 41e is a water tightness keeping surface configured by a slant surface. The outer circumferential protruded portion 46e and the outer circumferential slant surface 46g which are provided on the protruded portion 46c abut on and are disposed in the second disposition portion 41e. An inside diameter of the first disposition portion 41d is set to be larger by a predetermined dimension than an outside diameter dimension of the protruded portion 46c.

A small diameter portion 41f is formed on an outer circumferential face of the first case connecting member 41. A male screw portion 41m is provided on an outer circumferential face of the small diameter portion 41f. The male screw portion 41m is screwed into the female screw portion 16f shown in FIG. 6 which is provided on an inner surface of the second housing space 16.

Reference numeral 41g designates an O-ring. The O-ring 41g is disposed in an annular recessed portion 41h which is formed on a raised surface of the first case connecting member 41.

Here, assembly of the cable portion group 40 will be described.

Upon connection of the first connector case 11 and the first case connecting member 41, an operator firstly inserts the integral cable 42 into the space portion 14 of the first connector case 11. More specifically, the operator extends a distal end side of the integral cable 42 from the opening 15*a* through the extension hole 13*a* and the space portion 14. Thereafter, the operator moves the first connector case 11 to the direction of the bend preventing portion 46 along the electric cable 45. Subsequently, the operator disposes the first connector case 11 in close vicinity to the support member 48 which is integrally fixed to the electric cable 45 via the fixing section 47.

Further, the operator moves the first case connecting member 41 which is disposed on the electric cable 45 to the direction of the bend preventing portion 46 along the electric cable 45. Subsequently, the operator disposes the protruded portion 46*c* of the bend preventing portion 46 in the recessed portion 41*a*.

Next, the operator shifts to an operation of connecting the first connector case 11 and the first case connecting member 41. Therefore, the operator firstly brings the bottom surface of the recessed portion 41*a* into close vicinity to the raised surface 46*h*. Thereupon, the annular protruded portion 41*c* which is provided on the bottom surface abuts on the raised surface 46*h*, and the outer circumferential protruded portion 46*e* of the bend preventing portion 46 abuts on the water tightness keeping surface of the second disposition portion 41*e*.

Next, the operator moves the connecting portion 13 of the first connector case 11 to the small diameter portion 41*f* of the first case connecting member 41. Subsequently, the operator fits the inner surface of the second housing space 16 onto the outer circumferential face of the large diameter portion 48*c* of the support member 48. Thereafter, in the state, the connecting portion 13 is brought into close vicinity to the small diameter portion 41*f*. Thereupon, the female screw portion 16*f* and the male screw portion 41*m* abut on each other.

Here, the operator holds, for example, the first connector case 11 with one hand, and rotates the first case connecting member 41 in a predetermined direction with the other hand. Subsequently, the operator brings the female screw portion 16*f* and the male screw portion 41*m* into a screwed state. Thereafter, the operator increases a screwed length by hand operation, and finally brings about a predetermined screwed state.

On the above occasion, the connection portion side end surface of the first connector case 11 is to approach the O-ring 41*g* which is disposed in the annular recessed portion 41*h* of the first case connecting member 41. Thereafter, the O-ring 41*g* is brought into close contact with the connection portion side end surface of the first connector case 11. In addition, the annular protruded portion 41*c* is brought into close contact with the raised surface 46*h*, and the second disposition portion 41*e* is brought into close contact with the outer circumferential protruded portion 46*e*.

Subsequently, when the predetermined screwed state shown in FIG. 6 is brought about, the cable portion group 40 in which the first case connecting member 41 to which the first connector case 11 is connected is integrally fixed to the bend preventing portion 46 is configured. In the cable portion group 40, the O-ring 41*g* is crushed, and the connection portion side end surface of the first connector case 11 and the raised surface on which the first case connecting member 41 is disposed are brought into close contact with each other. Further, the end surface of the small diameter portion 48*b* of the support member 48 holds the end surface 46*f* of the bend preventing portion 46, whereby the annular protruded portion 41*c* is pressed to the raised surface 46*h*. As a result, the bottom surface of the recessed portion 41*a* is brought into close contact with the raised surface 46*h*, and the outer circumferential protruded portion 46*e* is crushed to bring the outer circumferential slant surface 46*g* into close contact with the water tightness keeping surface of the second disposition portion 41*e*.

Thereupon, water tightness between the first connector case 11 and the first case connecting member 41, and water tightness between the first case connecting member 41 and the bend preventing portion 46 configuring the integral cable 42 are kept.

The second connector case 21 and the second case connecting member 22 which configure the aforementioned connection cable 4 are integrally fixed to the bend preventing portion 46 of the integral cable 42 with water tightness being kept similarly to the first connector case 11 and the first case connecting member 41.

Figure 7:
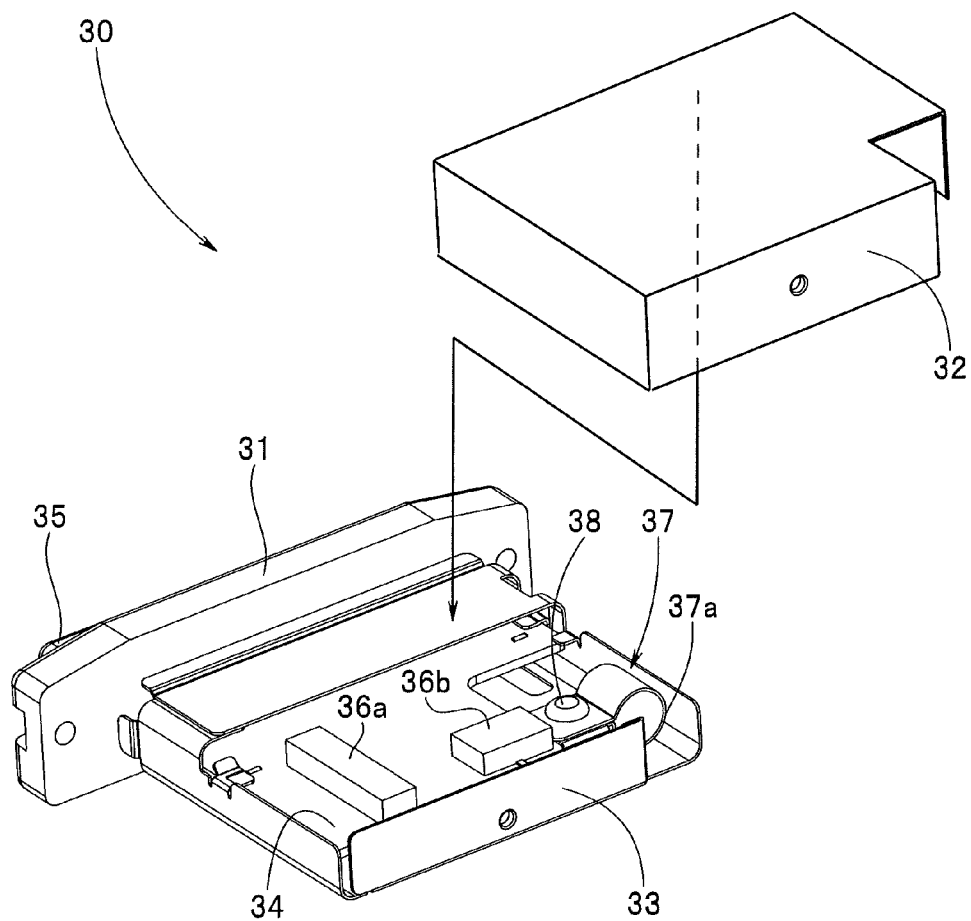
FIG. 7 is a view explaining a terminal portion group.

With reference to FIGS. 3 and 7, the terminal portion group 30 will be described.

The terminal portion group 30 is an electric connection portion, and is configured by mainly including a terminal portion 31, a shield cover 32, a shield main body 33 and a circuit board 34.

The terminal portion 31 is a case body in a rectangular shape which is formed of a rigid resin member, and includes a connecting portion 35 having a plurality of electric contacts.

In the circuit board 34, for example, printed wiring (not illustrated) is provided, at least one electronic component (not illustrated) is mounted, and a desired circuit is configured. The printed wiring and the electric contacts of the connecting portion 35 are electrically connected.

The circuit board 34 has, for example, female connectors 36*a* and 36*b* which are signal line connecting portions. Further, the circuit board 34 has a cable fixing portion 37 for mounting and fixing a distal end portion of the electric cable 45 which configures the integral cable 42 to the circuit board 34. The cable fixing portion 37 is fixed to the circuit board 34 so that the end portion of the electric cable 45 is disposed at one side surface side of the terminal portion 31.

The cable fixing portion 37 is fixed to the circuit board 34 by a mounting screw 38. The female connectors 36*a* and 36*b* are board-side connectors to which the male connectors 43*a* and 43*b* are connected.

The signal line 44*a* which is inserted through the inside of the electric cable 45 is connected to the circuit board 34 by the first male connector 43*a* being connected to the first female connector 36*a*, and the second male connector 43*b* being connected to the second female connector 36*b*. After the connection, a distal end portion of the electric cable 45 is disposed in a ring portion 37*a* of the cable fixing portion 37, and the mounting screw 38 is fastened. Thereby, the distal end portion of the electric cable 45 is fixed to the circuit board 34 to be located at one side surface side of the terminal portion 31. In the fixed state, a load is prevented from being directly transmitted to the signal line 44*a* even when a tensile force is applied to the electric cable 45.

In the present embodiment, the circuit board 34 is held by the shield main body 33 as shown in FIG. 7. The shield cover 32 is put on the shield main body 33, whereby a shield case 39 is configured, and the circuit board 34 is covered with the shield case 39. In the state, the electronic component and the printed wiring which are mounted on the circuit board 34 are in a state in which the electronic component and the printed wiring are apart from the shield cover 32 and the shield main body 33 by a predetermined distance. Accordingly, the circuit on the circuit board 34 is shut off from the outside by the shield case 39, and the circuit on the circuit board 34 avoids being influenced by external noise, and giving noise to the outside.

Figure 8:
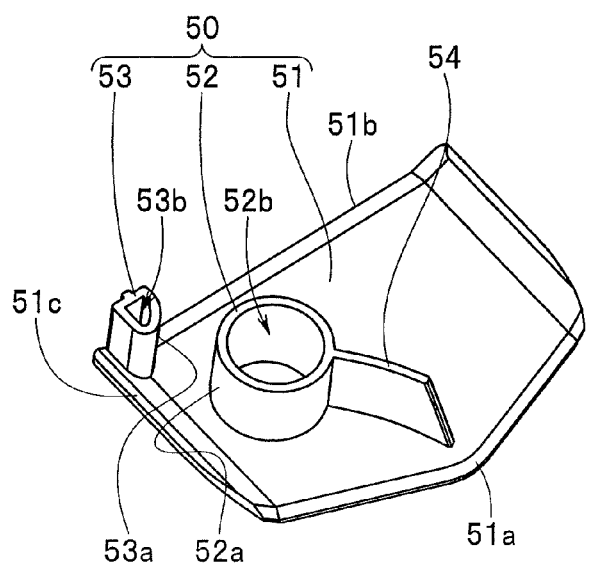
FIG. 8 is a view explaining a slide member.

With reference to FIGS. 3 and 8, the slide member 50 will be described.

The slide member 50 is formed of a rigid resin member excellent in slidability, and is configured by including a first protruded portion 52 and a second protruded portion 53 in a plate-shaped slide main body 51. The slide member 50 is slidably disposed in the first housing space 15 of the housing portion 12 which configures the first connector case 11.

The slide main body 51 is substantially in, for example, a shape of a baseball home plate. The slide main body 51 includes the first protruded portion 52 and the second protruded portion 53 both in a columnar shape with a predetermined height dimension on a cable disposition surface which is one surface side. The slide member 50 is disposed in the first housing space 15 through the opening 15a from an apex portion 51a side of the slide main body 51. A width dimension of the slide main body 51 is set to be smaller by a predetermined dimension than a width dimension of the first housing space 15 with in consideration of slidability.

According to the configuration, the slide member 50 smoothly moves inside the first housing space 15 from the opening 15a to a depth direction to be housed.

The first protruded portion 52 and the second protruded portion 53 are cable bending shape defining portions. The protruded portions 52 and 53 define a cable disposition position on one surface side and a bending shape, and bring the electric cable 45 housed in the first housing space 15 into, for example, a substantially S-shape which is a bending shape set in advance.

The first protruded portion 52 is provided at the apex portion 51a side of the slide main body 51 to be located at an extension hole 13a side from the second protruded portion 53, in the state in which the slide member 50 is disposed in the first housing space 15.

The first protruded portion 52 is configured by, for example, a column portion in a cylindrical shape. In the first housing space 15, the first protruded portion 52 bends the electric cable 45 which is extended to the first housing space 15 from the extension hole 13a to be disposed along, for example, a side wall at one side (see reference sign 15b of FIG. 3) in the first housing space 15. Further, the first protruded portion 52 bends the electric cable 45 disposed at the side wall 15b at one side toward a side wall 15c at the other side along a peripheral surface 52a of the column portion.

Therefore, a radius of the peripheral surface 52a of the first protruded portion 52 is set in consideration of sturdiness of the electric cable 45, namely, so as to bend the electric cable 45 with a predetermined curvature or less without folding the electric cable 45. A center position of the first protruded portion 52 is set at a position which is apart by a predetermined distance from a perpendicular shown by the two-dot chain line to a side 51c at one side in consideration of the diameter of the electric cable 45.

The electric cable 45 is disposed at the side of the side 51c at one side of the peripheral surface 52a. The perpendicular is drawn from the apex portion 51a to one side 51b opposed to the apex portion 51a. The side 51c at one side is one of the sides at both ends perpendicular to the one side 51b.

In the present embodiment, the peripheral surface 52a is a circumferential surface of the first protruded portion 52. However, the peripheral surface 52a is not limited to a circumferential surface, and may be a peripheral surface or the like which is provided in a predetermined range of, for example, a rectangular column. Further, a shape of reference sign 52b is a deformation preventing shape at the time of molding. Due to the presence of the deformation preventing shape 52b, deformation to be a sink and rib effect can be prevented, and slidability of a sliding surface of the slide main body 51 and the first housing space 15 is improved.

The second protruded portion 53 is a columnar portion having, for example, a curved surface portion 53a, and includes a deformation preventing shape 53b. The second protruded portion 53 restricts the electric cable 45 from protruding outside from the one side 51b. Further, the second protruded portion 53 abuts on the electric cable 45 which bends to the side wall 15b at one side of the first housing space 15 by the first protruded portion 52, butts the electric cable 45 against the peripheral surface 52a of the first protruded portion 52, and changes the bending direction of the electric cable 45 to the side wall 15c at the other side.

Therefore, the curved surface portion 53a of the second protruded portion 53 is an abutment surface which abuts on the electric cable 45. A center of the curved surface portion 53a of the second protruded portion 53 is located at the one side 51b side and at the side of the side 51c at one side, from the center of the first protruded portion 52. Further, a separation distance between the curved surface portion 53a and the peripheral surface 52a is set at a distance which is set in advance in consideration of the diameter dimension and sturdiness of the electric cable 45.

More specifically, a separation distance between the first protruded portion 52 and the second protruded portion 53 is a value obtained by adding a predetermined clearance to the diameter dimension of the electric cable 45. The slide member 50 is slid from the opening 15a in the first housing space 15 to the depth direction in a state in which the electric cable 45 is disposed between the first protruded portion 52 and the second protruded portion 53. In the slide member 50 in which the separation distance between the first protruded portion 52 and the second protruded portion 53 is set at the value, the electric cable 45 smoothly slides without being locked between the curved surface portion 53a and the peripheral surface 52a while sliding. Further, the electric cable 45 smoothly slides while keeping a state bending toward the side wall 15c at the other side, without being laid out of the one side 51b side.

Reference sign 54 is a separation plate. The separation plate 54 guides the electric cable 45, which is extended from the extension hole 13a to the first housing space 15, to the side of the side 51c at one side. Further, the separation plate 54 prevents the electric cables in bending shapes from directly contact each other on the cable disposition surface.

Here, assembly of the cable 4A will be described.

Figure 9:
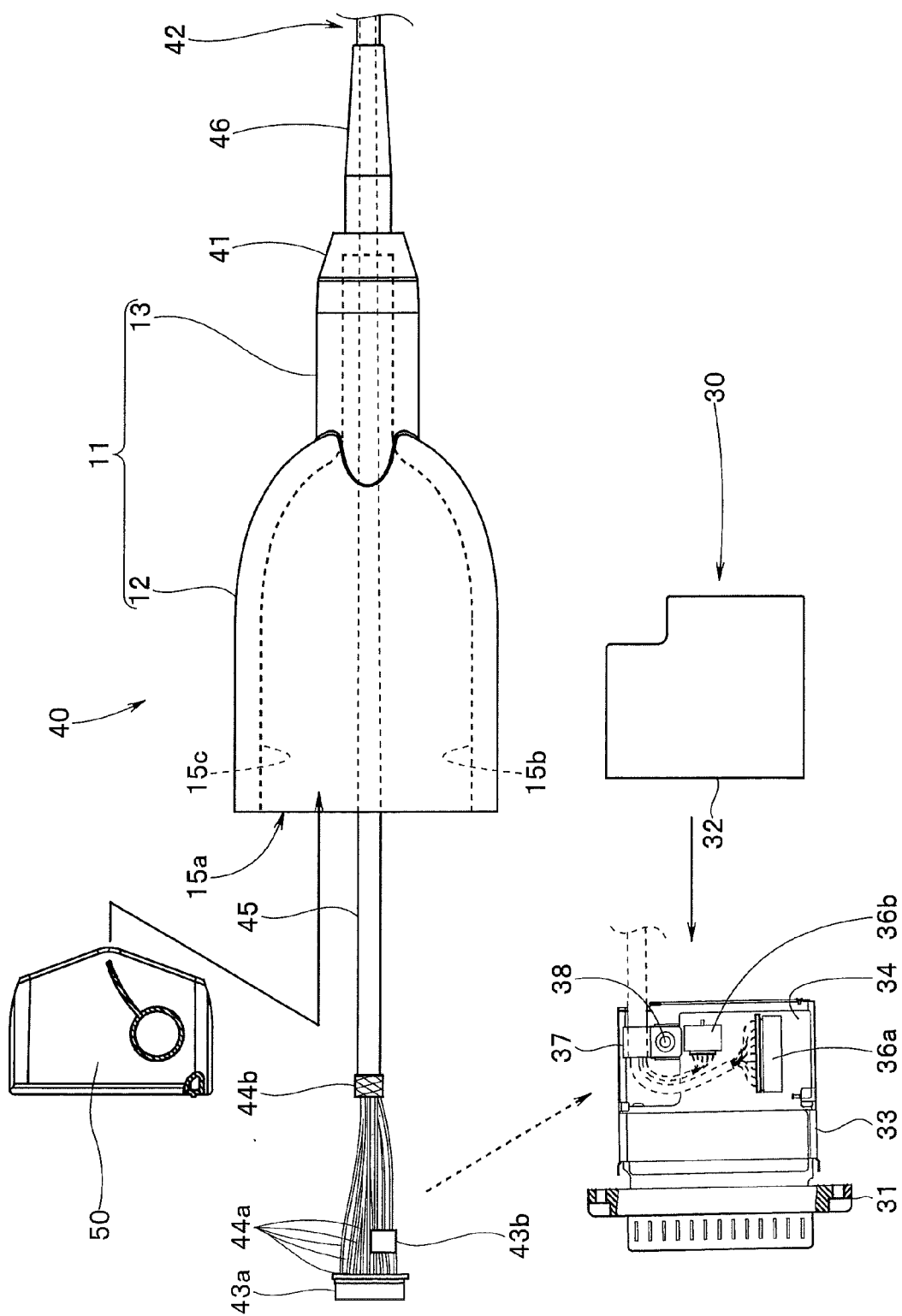
FIG. 9 is a view explaining respective portions prepared for assembling the cable, and explaining a procedure of connecting a connector of an electric cable to a connector of a board.

Upon assembly of the cable 4A, an operator first prepares the terminal portion group 30, the cable portion group 40 and the slide member 50 which are shown in FIG. 9.

Subsequently, the operator puts the ring portion 37a of the cable fixing portion 37 on the distal end portion of the electric cable 45 which is extended by a predetermined length from the opening 15a of the first connector case 11. Thereafter, the operator connects the first male connector 43a to which the signal lines 44a exposed from the distal end of the electric cable 45 are connected as shown by the broken lines in FIG. 9 to the first female connector 36a. Further, the operator connects the second male connector 43b to which the signal lines 44a are connected, to the second female connector 36b. After the connection, the operator disposes the cable fixing portion 37 at the circuit board 34. Subsequently, the operator fixes the cable fixing portion 37 to the circuit board 34 by the mounting screw 38, and integrally fixes the distal end portion of the electric cable 45 to the cable fixing portion 37.

Thereafter, the operator puts the shield cover 32 on the shield main body 33, and disposes the circuit board 34 in the shield case 39.

Figure 10:
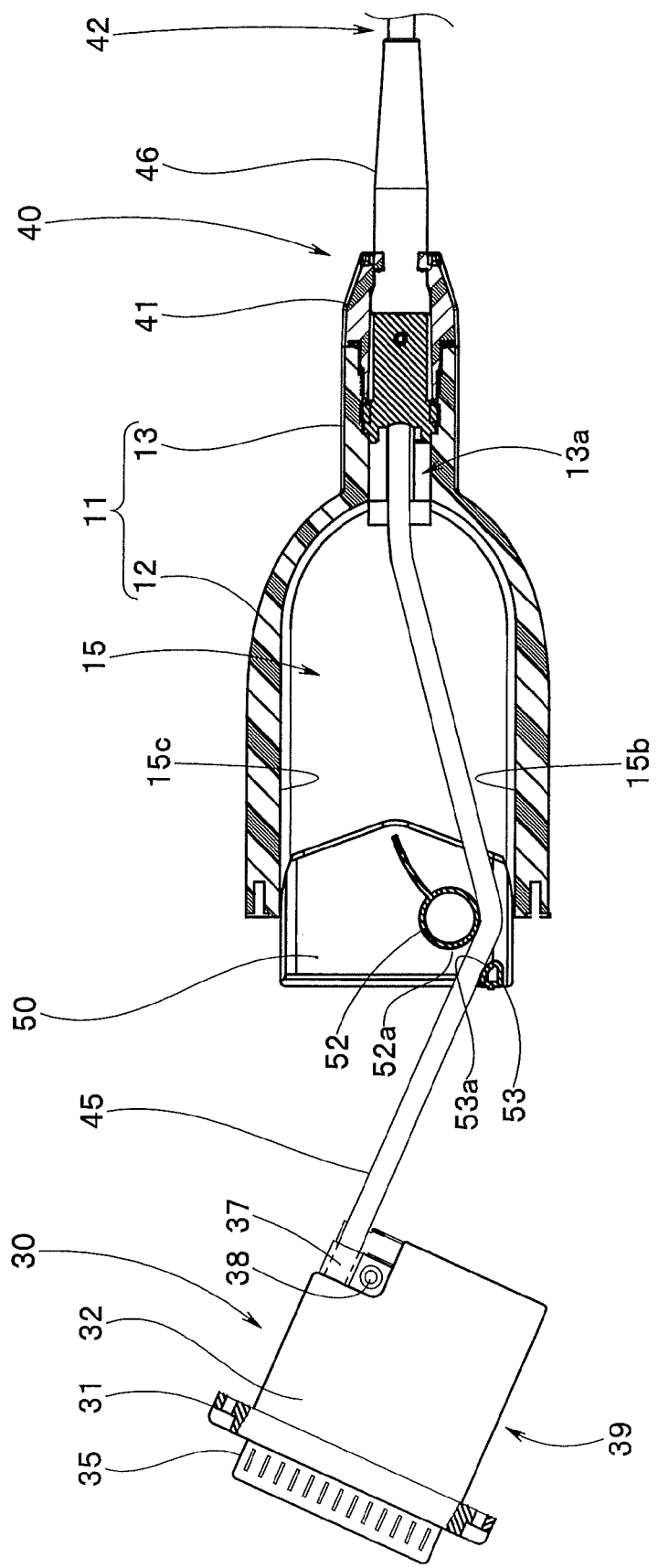
FIG. 10 is a view explaining a state in which a slide member is disposed in a first housing space and a direction of the cable extended into the first housing space is defined in one side wall direction, in order to house the cable and a shield case in the first housing space.

Next, the operator disposes the slide member 50 in the first housing space 15. At the occasion, the operator disposes the electric cable 45 between the peripheral surface 52a of the first protruded portion 52 and the curved surface portion 53a of the second protruded portion 53 as shown in FIG. 10. Subsequently, in the disposition state, the operator disposes the apex portion 51a side of the slide main body 51 in the first housing space 15 through the opening 15a.

Thereupon, the electric cable 45 which is extended from the extension hole 13a into the first housing space 15 abuts on the peripheral surface 52a at the side of the side 51c at one side of the first protruded portion 52, and is disposed toward the side wall 15b at one side within the first housing space 15.

Next, the operator disposes a shield case end surface 39a which configures the terminal portion group 30 in close vicinity to the one side 51b of the slide main body 51 which protrudes from the opening 15a of the first housing space 15 while facing the one side 51b. At this time, the operator disposes the distal end portion of the electric cable 45 at the side of the side wall 15c at the other side away from the first protruded portion 52 of the slide main body 51 which is disposed in the first housing space 15. As a result, bending is formed in the electric cable 45, and bending substantially in an S-shape is formed at the distal end side of the cable, while the tolerance at the time of production of the electric cable 45 is absorbed in the substantially S-shape.

Figure 11A:
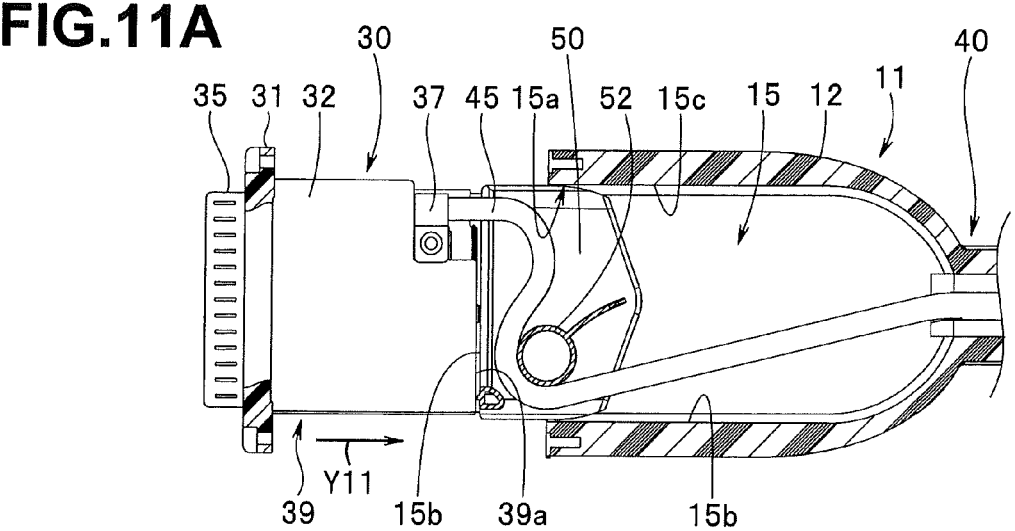
FIG. 11A is a view showing a housing start state in which the shield case is disposed in close vicinity to the slide member disposed in the first housing space in order to house the cable and the shield case in the first housing space.
Figure 11B:
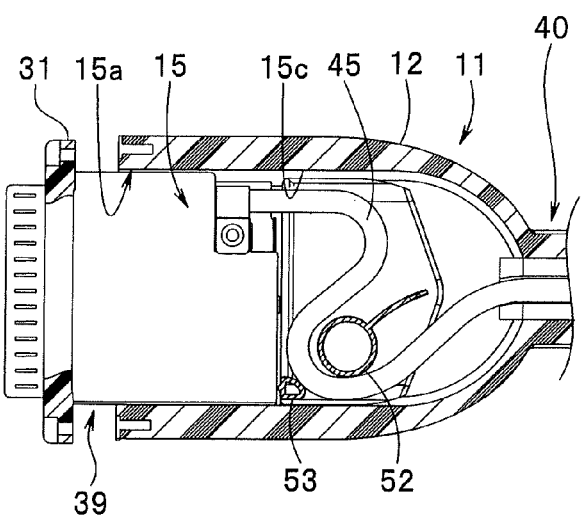
FIG. 11B is a view explaining a state in which the cable and the shield case are being housed in the first housing space.

Next, the operator performs an operation of housing the shield case 39 which configures the terminal portion group 30 into the first housing space 15. More specifically, the operator moves the shield case 39 to an arrow Y11 direction of FIG. 11A. Thereupon, with movement of the terminal portion group 30, the apex portion 51a of the slide main body 51 is moved in the depth direction of the first housing space 15, and the shield case 39 is gradually housed into the first housing space, as shown in FIG. 11B.

At the time, the electric cable 45 moves between the curved surface portion 53a and the peripheral surface 52a with movement of the slide main body 51 while abutting on the curved surface portion 53a of the second protruded portion 53, and the cable bending shape of the cable 45 gradually changes into a desired S-shape. More specifically, with the aforementioned movement, the electric cable 45 is butted to the peripheral surface 52a at the opposite side from the peripheral surface 52a at the side of the side 51c at one side on which the cable 45 abuts, while the center of the first protruded portion 52 is interposed therebetween, and bends toward the side wall 15c at the other side.

Figure 11C:
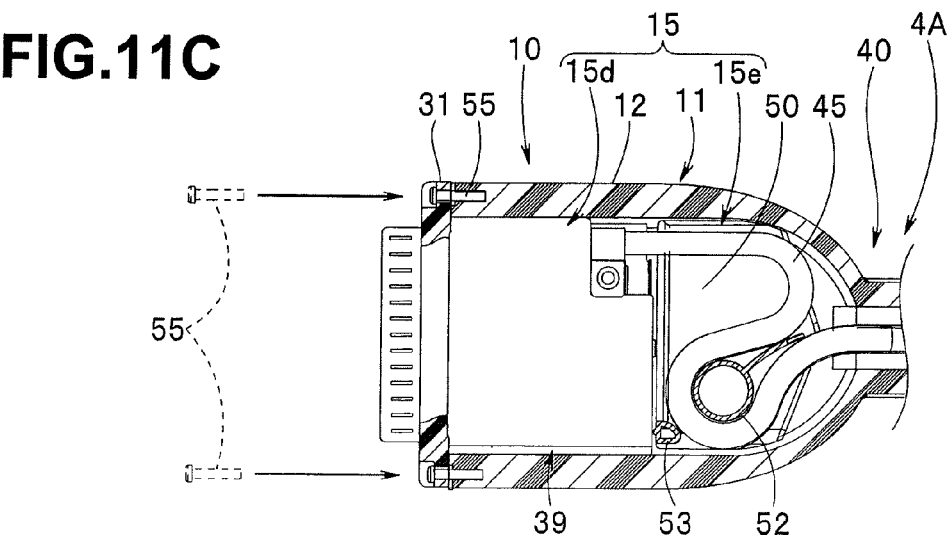
FIG. 11C is a view explaining a state in which the cable and the shield case are housed in the first housing space, and the connector configured by the terminal portion being integrally fixed to the connector case by integral fixing screws and the cable including the connector.

Subsequently, the operator continues to house the shield case 39 into the first housing space 15. As a result, a surface at the opening 15a side, of the terminal portion 31 which configures the terminal portion group 30 abuts on a distal end face of the opening 15a of the housing portion 12 which configures the first connector case 11, as shown in FIG. 11C.

Thereby, the shield case 39 is housed in the shield case housing region 15d in the first housing space 15. At this time, the electric cable 45 is housed in the slide member housing region 15e in the first housing space 15 by being bent and deformed in a desired S-shape.

Thereafter, operation is performed to fix the terminal portion 31 to the distal end face of the opening 15a of the housing portion 12 by screwing integral fixing screws 55 shown by the broken lines. Thereby, the first connector 10 is formed, and the cable 4A is configured.

In the fixed state, a water tightness keeping member which is disposed like an O-ring and keeps water tightness, is provided between the terminal portion 31 and the opening 15a side distal end face of the first connector case 11.

In this manner, when the terminal portion of the terminal portion group is assembled to the connector case of the cable portion group to form the connector, the slide member which is slidable with respect to the housing space of the connector case and including the cable bending shape defining portion is disposed in the housing space in advance, and the electric cable is disposed in the cable bending shape defining portion. As a result, the electric cable can be easily housed by being bent and deformed into the S-shape, which is set in advance, in the slide member housing region, with the movement of the slide member.

According to the configuration, operation of providing a curving form to the cable can be made unnecessary, and the extension length of the cable which is extended from the opening of the connector case can be set in advance in consideration of operability and housing easiness. In addition, the extension length of the cable which is extended from the opening of the connector case can be set in advance, whereby the connector case can be water-tightly fixed to the cable in advance.

Here, the result of the assembly experiment in the case of use of only the first protruded portion 52 for the cable bending shape defining portion provided in the slide member 50 will be described.

Figure 12:
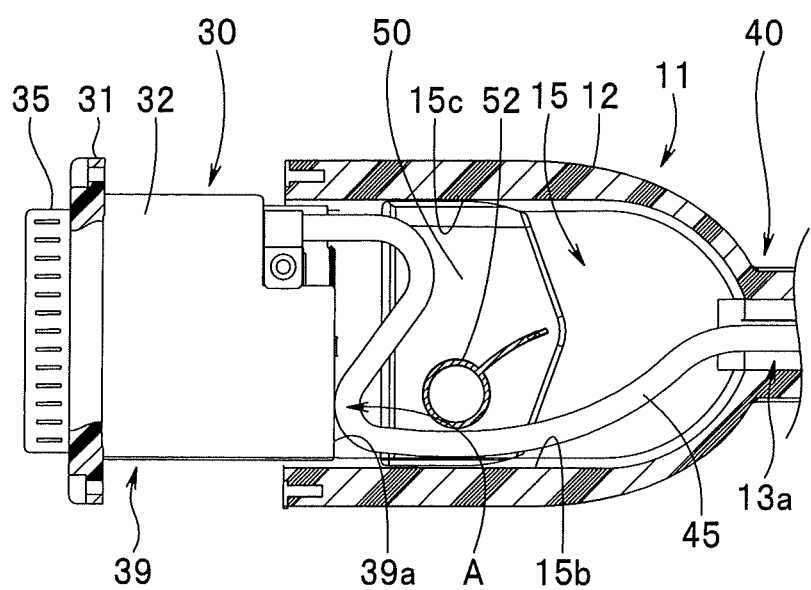
FIG. 12 is a view showing an action due to bracing which occurs when the slide member with only a first protruded portion provided at a cable main body is disposed in the first housing space, and the cable and the shield case are housed in the first housing space.

When the electric cable 45 and the shield case 39 of the terminal portion group 30 are disposed in the first housing space 15, and the terminal portion group 30 is moved to the depth direction of the first housing space 15 as in the above description, in the case of use of only the first protruded portion 52 for the cable bending shape defining portion, the electric cable 45 braces in an A part as shown in FIG. 12, and it becomes difficult to further house the terminal portion group 30. Further, in the state, when the operator takes his or her hand off the terminal portion group 30, the terminal portion group 30 is pushed out of the first housing space 15 by the repulsive force of the electric cable 45.

Accordingly, when the cable bending shape defining portion is configured by only the first protruded portion, on the occasion of disposition of the electric cable 45 and the terminal portion group 30 in the first housing space 15, a curving form for obtaining the desired bending shape needs to be applied to the electric cable 45 in advance. However, even when the curving form is applied, if the curving form is deformed by the repulsive force which the electric cable 45 has when the terminal portion group 30 is moved to the depth direction of the first housing space 15, it becomes impossible to deform the electric cable 45 into the desired bending shape, bracing as in the A part described above occurs, and housing the terminal portion group 30 in the first housing space 15 is difficult.

The present invention is not limited only to the embodiment described above, and can be carried out by being variously modified within the range without departing from the gist of the invention. For example, the present embodiment is a rigid endoscope, but may be a flexible endoscope in which an insertion portion has flexibility as a matter of course.

What is claimed is:

1. A connector, comprising:
a cable including a plurality of signal lines which are combined into one;
an electric connecting portion that includes a case body in a rectangular shape and a circuit board, and has, on the circuit board, a signal line connecting portion connected to a signal line exposed from the cable, and a cable fixing portion to which a distal end portion of the cable is fixed;
a flat-type connector case of an integral structure that has a housing space housing the electric connecting portion and the cable, an opening in which the case body of the electric connecting portion is integrally mounted, and an extension hole from which the cable is extended into the housing space, and is integrally fixed to an intermediate portion of the cable; and a slide member that is slidably disposed in the housing space of the connector case, and includes, on one surface side, a cable bending shape defining portion that defines a bending shape of the cable which is housed in the housing space.

2. The connector according to claim 1, wherein, in the cable integrally fixed to the connector case, an extension length by which the cable extends from the opening of the connector case is set in advance.

3. A connector, comprising:

a cable portion group including a connector case of an integral structure in a flat shape that is integrally fixed to an intermediate portion of a cable having a plurality of signal lines which are combined into one, and at least one cable side connector connected to the plurality of signal lines which are exposed from an end surface of the cable extended by a predetermined length from an opening in a rectangular shape via a housing space included by the connector case;

a terminal portion group including a case body in a rectangular shape fixedly provided in the opening, and a board mounting a board-side connector to which the cable side connector is connected, and having a cable fixing portion to which a distal end portion of the cable is fixed; and a slide member that is slidably disposed in the housing space of the connector case, and includes a cable bending shape defining portion that deforms the cable in a state in which the cable side connector is connected to the board-side connector of the board, into a predetermined bending shape and houses the cable in the housing space.

4. The connector according to claim 1, wherein the cable bending shape defining portion is configured by a first protruded portion and a second protruded portion that are provided at predetermined positions at a side of one side on the one surface side.

5. The connector according to claim 4, wherein the first protruded portion is a columnar portion including a peripheral surface that bends the cable with a predetermined curvature or less, is provided at a side of the extension hole from the second protruded portion, and bends the cable extended into the housing space from the extension hole to a predetermined direction in the housing space.

6. The connector according to claim 5, wherein the second protruded portion is a columnar portion including a curved surface portion that abuts on the cable, is provided further at the side of the one side from the first protruded portion so that a separation distance between the curved surface portion and the peripheral surface becomes a predetermined distance, and causes the cable which is bent toward the predetermined direction in the housing space by the first protruded portion to abut on the curved surface portion to bend the cable toward a direction of the first protruded portion.

7. The connector according to claim 1, wherein the cable fixing portion of the electric connecting portion is provided at a position in which a distal end portion of the cable is disposed on one side surface side of the case body.

* * * * *